United States Patent
Jaber et al.

(10) Patent No.: US 11,676,707 B2
(45) Date of Patent: Jun. 13, 2023

(54) CLASSIFICATION BASED ON CHARACTERIZATION ANALYSIS METHODS AND SYSTEMS

(71) Applicants: NantOmics, LLC, Culver City, CA (US); NantHealth, Inc., Culver City, CA (US)

(72) Inventors: Mustafa Jaber, Los Angeles, CA (US); Liudmila A Beziaeva, Culver City, CA (US); Christopher W Szeto, Scotts Valley, CA (US); Bing Song, La Canada, CA (US)

(73) Assignees: NantOmics, LLC, Culver City, CA (US); Nant Health, Inc., Culver City, CA (US)

( * ) Notice: Subject to any disclaimer, the term of this patent is extended or adjusted under 35 U.S.C. 154(b) by 0 days.

(21) Appl. No.: 17/539,292

(22) Filed: Dec. 1, 2021

(65) Prior Publication Data
US 2022/0092340 A1    Mar. 24, 2022

Related U.S. Application Data

(63) Continuation of application No. 16/685,191, filed on Nov. 15, 2019, now Pat. No. 11,195,062.
(Continued)

(51) Int. Cl.
*G06K 9/00*    (2022.01)
*G16H 30/40*    (2018.01)
(Continued)

(52) U.S. Cl.
CPC ......... *G16H 30/40* (2018.01); *G06F 18/2431* (2023.01); *G06N 3/04* (2013.01);
(Continued)

(58) Field of Classification Search
CPC ..................................................... G06K 9/628
See application file for complete search history.

(56) References Cited

U.S. PATENT DOCUMENTS 7,274,810 B2    9/2007    Reeves et al.
9,141,756 B1 *    9/2015    Hillis ...................... G16B 5/00
(Continued)

FOREIGN PATENT DOCUMENTS

| WO | 2015054666 A1 | 4/2015 |
| WO | 2019055555 A1 | 3/2019 |
| WO | 2019143633 A1 | 7/2019 |

OTHER PUBLICATIONS

Xie, Weidi, J. Alison Noble, and Andrew Zisserman. "Microscopy cell counting and detection with fully convolutional regression networks." Computer methods in biomechanics and biomedical engineering: Imaging & Visualization 6.3 (2018): 283-292. (Year: 2018).*
(Continued)

*Primary Examiner* — Hadi Akhavannik
(74) *Attorney, Agent, or Firm* — Frederick H. Gribbell; Russell F. Gribbell; Joseph L. Ulur

(57) ABSTRACT

A method at a computing device for classifying elements within an input, the method including breaking the input into a plurality of patches; for each patch: creating a vector output; applying a characterization map to select a classification bin from a plurality of classification bins; and utilizing the selected classification bin to classify the vector output to create a classified output; and compiling the classified output from each patch.

21 Claims, 17 Drawing Sheets

Related U.S. Application Data

(60) Provisional application No. 62/822,427, filed on Mar. 22, 2019, provisional application No. 62/767,955, filed on Nov. 15, 2018.

(51) Int. Cl.
| | |
|---|---|
| *G06T 7/00* | (2017.01) |
| *G06T 7/10* | (2017.01) |
| *G06N 3/04* | (2023.01) |
| *G16H 30/20* | (2018.01) |
| *G16H 50/20* | (2018.01) |
| *G06F 18/2431* | (2023.01) |
| *G06V 20/69* | (2022.01) |

(52) U.S. Cl.
CPC .............. *G06T 7/0012* (2013.01); *G06T 7/10* (2017.01); *G06V 20/698* (2022.01); *G16H 30/20* (2018.01); *G16H 50/20* (2018.01); *G06T 2207/20084* (2013.01); *G06T 2207/30024* (2013.01); *G06T 2207/30096* (2013.01)

(56) References Cited

U.S. PATENT DOCUMENTS

| | | | |
|---|---|---|---|
| 9,466,009 | B2 | 10/2016 | Jaber et al. |
| 2010/0088264 | A1* | 4/2010 | Teverovskiy .......... G16H 50/20 706/46 |
| 2014/0163389 | A1* | 6/2014 | Kudenov ............. A61B 5/0071 600/476 |
| 2016/0263187 | A1 | 9/2016 | Lander et al. |
| 2016/0307071 | A1* | 10/2016 | Perronnin ............ G06V 10/454 |
| 2017/0035381 | A1* | 2/2017 | Madabhushi ............ A61B 5/08 |
| 2017/0137806 | A1* | 5/2017 | Jaitin ................... C12Q 1/6809 |
| 2018/0059396 | A1* | 3/2018 | Chiang ............... G06V 10/443 |
| 2018/0204111 | A1* | 7/2018 | Zadeh ..................... G06N 3/043 |
| 2019/0285752 | A1* | 9/2019 | Chattopadhyay ..... G01S 17/931 |

OTHER PUBLICATIONS

Yu, K.-H et al, "Predicting non-small cell lung cancer prognosis by fully automated microscopic pathology image features," Nature Communications, Aug. 16, 2016, vol. 7 article No. 12474.

Coudray, N et al, "Classification and mutation prediction from non-small cell lung cancer histopathology images using deep learning," Nature Medicine, 2018, pp. 1559-1567, vol. 24.

Graham, S et al, "Classification of lung cancer histology images using patch-level summary statistics," Digital Pathology conference, Proceedings of International Society for Optics and Photonics, 2018, vol. 1058119.

International Searching Authority, Written Opinion of the International Searching Authority for International Application No. PCT/US2019/061704, dated Jan. 27, 2020.

Bentaieb, Aicha, "Analyzing Cancers in Digitized Histopathology Images," Thesis Submitted in Partial Fulfillment of the Requirements for the Degree of Doctor of Philosophy in the School of Computing Science Faculty of Applied Sciences at Simon Fraser University, Fall 2018.

\* cited by examiner

CLASSIFICATION BASED ON CHARACTERIZATION ANALYSIS METHODS AND SYSTEMS

CROSS REFERENCE TO RELATED APPLICATIONS

The present disclosure claims priority to U.S. Provisional Application No. 62/767,955, filed Nov. 15, 2018, the entire contents of which are incorporated herein by reference. The present disclosure further claims priority to U.S. Provisional Application No. 62/822,427, filed Mar. 22, 2019, the entire contents of which are incorporated herein by reference.

FIELD OF THE DISCLOSURE

The present disclosure relates generally to image processing, and in some embodiments relates to image processing for pathology applications.

BACKGROUND

The following description includes information that may be useful in understanding the present inventive subject matter. It is not an admission that any of the information provided herein is prior art or applicant admitted prior art, or relevant to the presently claimed inventive subject matter, or that any publication specifically or implicitly referenced is prior art or applicant admitted prior art.

Accurate classification of an image by a computer system could be useful in a variety of fields. For example, in pathology applications, whole slide imaging (WSI) may be used in a computer system to allow for classification of different cancer types. Whole slide imaging refers to the scanning of conventional glass slides to produce digital slides. Whole slide imaging is used by pathologists for diagnostic, educational, and research purposes.

Elements within an image may need to be categorized. For example, an image comprising tumor cells may include different types of cancer cells. For pathology it may be important to know the proportion of each of the different types of cancer cells. However, analysis of whole slide images utilizing conventional techniques does not always produce the most accurate categorization. Thus, there is still a need for computer analysis of images to produce more accurate categorization.

SUMMARY

The present disclosure provides a method at a computing device for classifying elements within an input, the method comprising: breaking the input into a plurality of patches; for each patch: creating a vector output; applying a characterization map to select a classification bin from a plurality of classification bins; and utilizing the selected classification bin to classify the vector output to create a classified output; and compiling the classified output from each patch.

In one embodiment, the method further includes applying a mask to the input prior to creating the vector input.

In one embodiment, the vector output is created using a convolutional neural network.

In one embodiment, each classification bin from the plurality of classification bins contains linear and non-linear classifiers.

In one embodiment, the linear and non-linear classifiers in each classification bin are optimized based on the characterization map.

In one embodiment, the characterization map is a density map of an element within the input, and wherein each of the plurality of classification bins corresponds to a different density range for the element.

In one embodiment, input is a whole slide image of a tumor and the characterization map is a cell density map.

In one embodiment, each classification bin contains linear and non-linear classifiers to identify between different types of cancer cells at a cell density level associated with the classification bin.

In one embodiment, the tumor is a non-small cell lung cancer and the different types of cancer cells include adenocarcinoma and squamous cell carcinoma cells.

In one embodiment, the method includes applying a tumor mask to the whole slide image.

In on embodiment the tumor is a breast cancer and the different types of cancer cells can be divided into two or more of: Luminal A, Luminal B, Triple-negative/basal-like, and HER2-enriched cells.

Another aspect of the present disclosure provides computing device for classifying elements within an input, the computing device comprising a processor configured to execute instructions to: break the input into a plurality of patches; for each patch: create a vector output; apply a characterization map to select a classification bin from a plurality of classification bins; and utilize the selected classification bin to classify the vector output to create a classified output; and compile the classified output from each patch.

Another aspect of the present disclosure provides a non-transitory computer readable medium for storing instruction code for classifying elements within an input, which, when executed by a processor of a computing device cause the computing device to: break the input into a plurality of patches; for each patch: create a vector output; apply a characterization map to select a classification bin from a plurality of classification bins; and utilize the selected classification bin to classify the vector output to create a classified output; and compile the classified output from each patch.

BRIEF DESCRIPTION OF THE DRAWINGS

The present disclosure will be better understood with reference to the drawings, in which.

DETAILED DESCRIPTION

Figure 1:
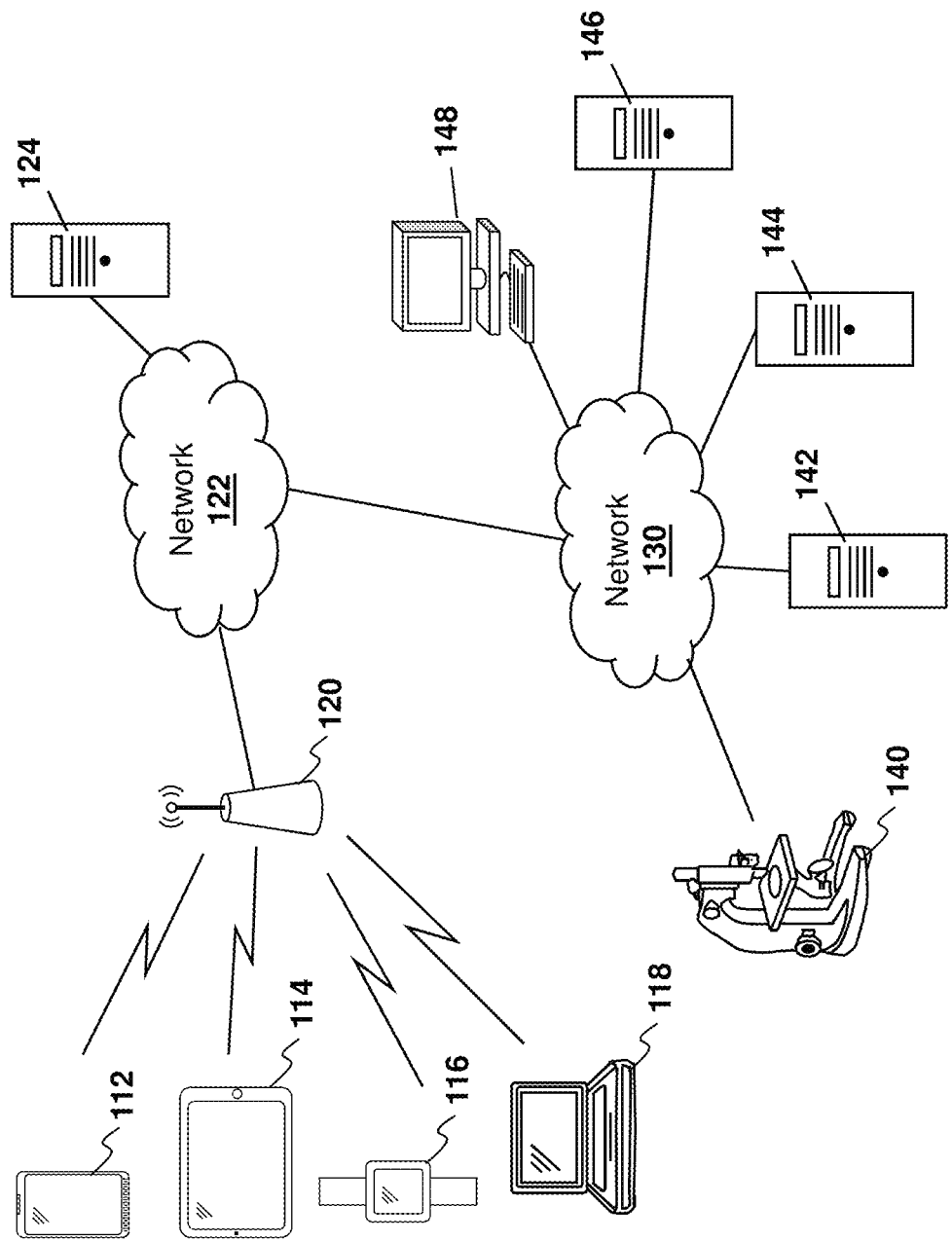
FIG. 1 is an architecture diagram showing example elements within a system capable of performing the embodiments of the present disclosure.

The various embodiments will now be described more fully herein with reference to the accompanying drawings, which form a part hereof, and which show, by way of illustration, specific examples of practicing the embodiments. This specification may, however, be embodied in many different forms and should not be construed as being limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment, or an embodiment combining software and hardware aspects. The following specification is, therefore, not to be taken in a limiting sense.

Throughout the specification and claims, the following terms take the meanings explicitly associated herein, unless the context clearly dictates otherwise:

The phrase "in one embodiment" as used herein does not necessarily refer to the same embodiment, though it may. Thus, as described below, various embodiments of the invention may be readily combined, without departing from the scope or spirit of the invention.

As used herein, the term "or" is an inclusive "or" operator, and is equivalent to the term "and/or," unless the context clearly dictates otherwise.

The term "based on" is not exclusive and allows for being based on additional factors not described, unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of a networked environment where two or more components or devices are able to exchange data, the terms "coupled to" and "coupled with" are also used to mean "communicatively coupled with", possibly via one or more intermediary devices.

In addition, throughout the specification, the meaning of "a", "an", and "the" includes plural references, and the meaning of "in" includes "in" and "on" unless the context clearly dictates otherwise.

Although some of the various embodiments presented herein constitute a single combination of inventive elements, it should be appreciated that the inventive subject matter is considered to include all possible combinations of the disclosed elements. As such, if one embodiment comprises elements A, B, and C, and another embodiment comprises elements B and D, then the inventive subject matter is also considered to include other remaining combinations of A, B, C, or D, even if not explicitly discussed herein. Further, the transitional term "comprising" means to have as parts or members, or to be those parts or members. As used herein, the transitional term "comprising" is inclusive or open-ended and does not exclude additional, unrecited elements or method steps.

Throughout the following discussion, numerous references will be made regarding servers, services, interfaces, engines, modules, clients, peers, portals, platforms, or other systems formed from computing devices. It should be appreciated that the use of such terms is deemed to represent one or more computing devices having at least one processor (e.g., ASIC, FPGA, DSP, x86, ARM, ColdFire, GPU, multi-core processors, etc.) configured to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable medium storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, a circuit-switched network, the Internet, LAN, WAN, VPN, or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

The embodiments of the present disclosure relate generally to categorization, and for some embodiments, to categorization of elements within an image. In some embodiments, the technology relates to histopathology, the microscopic examination of tissue for the purpose of determining whether the tissue is diseased and or studying diseased tissue. The tissue may be removed from any part of the body including, for example, breast lumps, specimens of bowel, kidney, liver, uterus lining, lung, chest, lymph node, muscle, nerve, skin, testicle, thyroid, or the like.

In some embodiments, the disclosed technology relates to identifying and distinguishing between different cancer cells within a digital histopathology image. The types of cancer in the cancer cells may include, but are not necessarily limited to, breast cancer, bladder cancer, brain cancer, lung cancer, pancreatic cancer, skin cancer, colorectal cancer, prostate cancer, stomach cancer, liver cancer, cervical cancer, soft the goal cancer, leukemia, non-Hodgkins lymphoma, kidney cancer, uterine cancer, bile duct cancer, bone cancer, ovarian cancer, gallbladder cancer, gastrointestinal cancer, oral cancer, throat cancer, ocular cancer, pelvic cancer, spinal cancer, testicular cancer, vegetable cancer, vulvar cancer, thyroid cancer. Further, the region of interest or classes may also be broader include abnormal tissue, benign tissue, malignant tissue, bone tissue, skin tissue, nerve tissue, intestinal tissue, muscle tissue, connective tissue, scar tissue, lymph avoid tissue, fat, epithelial tissue, nervous tissue, and blood vessels, among others.

When the embodiments involve tissues, tissues may be obtained from a subject in multiple settings, such as biopsy, surgery or autopsy. After tissues are removed from the subject, they may be prepared for chemical fixation by being placed in a fixative such as formalin to prevent the decay of the tissue. The tissues are then either frozen or set in molten wax. Sections of the tissues are then cut and placed on slides.

Once the tissue sections are on slides, a pathologist views the slides through a microscope to determine whether the issue is, for example, diseased, and if diseased, determine the stage of the disease. For example, a pathologist may determine whether the blood breast lump includes breast cancer cells and, if so, a pathologist may determine the grade and/or stage of cancer. Pathologists may also make determinations regarding tissue other than whether it is diseased. For example, a pathologist may determine the tissue includes lymphocytes. However, there is a technical problem with these determinations in that they are often unreliable, expensive, time-consuming, and generally require verification of multiple pathologists to minimize the likelihood of false determinations.

One solution to this technical problem is to use computer vision to determine a tissue characteristic, such as the type and/or grade of cancer by training a neural network or other machine learning system to determine whether the digital image tissues are diseased and determine characteristic of the diseased tissues, and to further categorize the tissues into different types of cancer cells. Computer vision relates to the automated extraction, analysis and understanding of useful information from one or more digital images. For example, computer vision may be used to determine the age of a person in a photograph by determining the location of the face of the person in a digital image, determining the location of the eyes of such person, and measuring the interpupillary distance of such person.

However, there is a technical problem with this approach in that, for example, the accuracy for categorization of different types of cancer cells may be inaccurate.

Some embodiments the present disclosure solve the above technical problem and provide a technical solution by using a density map on a patch of an image to apply different categorization or classification modules based on the density of that particular patch, resulting in more accurate categorization.

Environment

The embodiments of the present disclosure may be performed on one or more computing devices. In particular, the embodiments described below may be performed at a single computing device, or the computing may be distributed across a plurality of computing devices, were each computing device has varied functionality.

One example architecture is shown with regard to FIG. 1. FIG. 1 shows a plurality of computing devices or system components which may be used for the embodiments described below. However, the example of FIG. 1 is not limiting and in some cases fewer computing devices are used, in which case the remaining computing devices are omitted. In other cases, other computing devices not shown in FIG. 1 may be used with the embodiments of the present disclosure.

In the example of FIG. 1, various computing devices may communicate wirelessly. For example, a mobile device 112, tablet 114, peripheral 116 such as a wearable, or a laptop computer 118 may communicate with a network 122 through a wireless access point 120. Wireless access point 120 may be a cellular access point or a Wi-Fi access point, among other options.

A server 124 may further communicate with network 122. Network 122 may be any local or wide area network including, but not limited to the Internet.

Further, a network 130 may exist in some cases. Network 130 may be a local area network or a private wide area network, among other options. In other cases, network 130 may not exist and the various components shown in FIG. 1 that connect to network 130 may instead connect to network 122.

In the embodiment of FIG. 1, an optical microscope 140 may provide computing capabilities. For example, microscope 140 may include an ocular assembly, a camera, a slide platform, as well as components of a computing device 210 as described below in FIG. 2. Although the embodiment of FIG. 1 shows microscope 140 connected to a network 130, in some cases, microscope 140 can be directly coupled to a personal computer 148 or to servers 142, 144 or 146.

Further, servers 142, 144 and 146 may be configured to provide various computing functionality. Servers 142, 144 and 146 may include, for example, one or more application servers, content servers, search servers, Web servers, graphics processing unit (GPU) servers, and the like.

In some cases, one or more personal computers 148 may further provide computing functionality.

Computing Device

A computing device such as mobile device 112, tablet 112, peripheral 116, laptop 118, optical microscope 140, servers 124, 142, 144, or 146, or personal computer 148 may be used alone or in combination to perform the embodiments of the present disclosure. For example, one simplified computing device that may perform the embodiments described above is provided with regards to FIG. 2.

Figure 2:
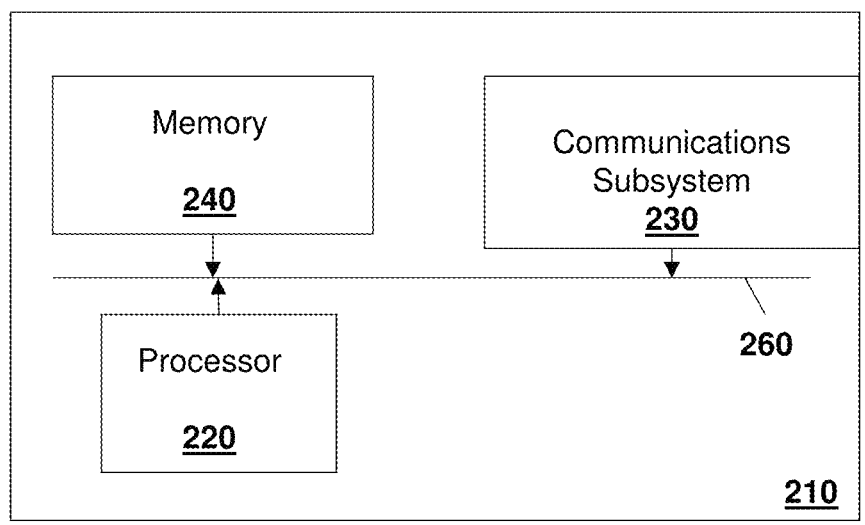
FIG. 2 is a block diagram of a simplified computing device capable of being used with the embodiments of the present disclosure.

In FIG. 2, computing device 210 includes a processor 220 and a communications subsystem 230, where the processor 220 and communications subsystem 230 cooperate to perform the methods of the embodiments described herein.

The processor 220 is configured to execute programmable logic, which may be stored, along with data, on the computing device 210, and is shown in the example of FIG. 2 as memory 240. The memory 240 can be any tangible, non-transitory computer readable storage medium, such as DRAM, Flash, optical (e.g., CD, DVD, etc.), magnetic (e.g., tape), flash drive, hard drive, or other memory known in the art. In one embodiment, processor 220 may also be implemented entirely in hardware and not require any stored program to execute logic functions.

Alternatively, or in addition to the memory 240, the computing device 210 may access data or programmable logic from an external storage medium, for example through the communications subsystem 230.

The communications subsystem 230 allows the computing device 210 to communicate with other devices or network elements.

Communications between the various elements of the computing device 210 may be through an internal bus 260 in one embodiment. However, other forms of communication are possible.

Classification System

Utilizing one or more of the computing devices described above, a classification system and the components thereof is now described. In some illustrated embodiments, the classification system may be used for purposes such as distinguishing between adenocarcinoma and squamous cell carcinoma lung cancers. However, in other embodiments, the classification system can be used for other pathological classifications such as for breast cancer classification, or for classification of other types of images including, but not limited to, population counts in urban mapping, vehicle control on roadways, forest fire prediction based on foliage density, among other applications.

Figure 3:
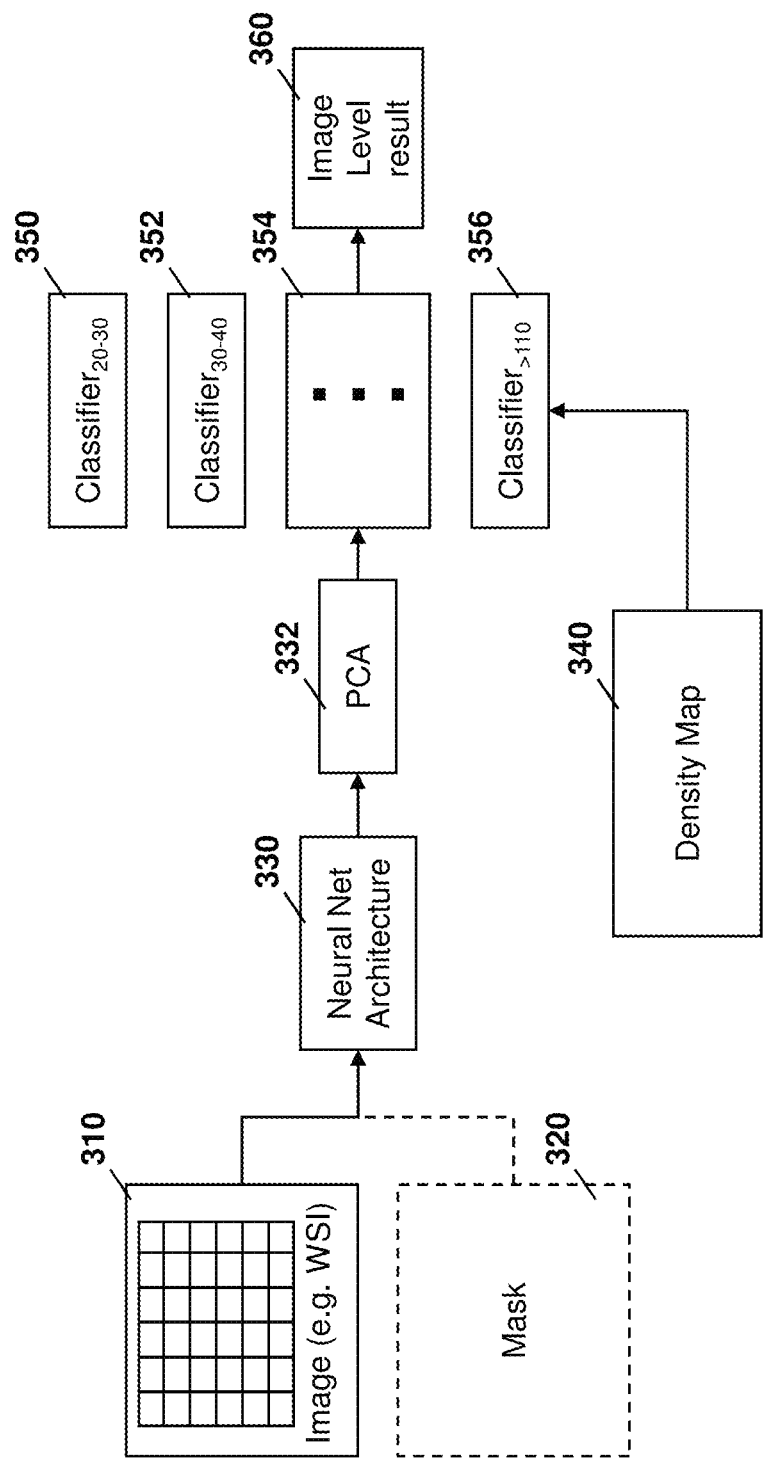
FIG. 3 is an example system diagram of the one system capable of being used for categorization of elements within an image.

In particular, reference is now made to FIG. 3. In the classification system of FIG. 3, an image 310 is used as the input image to the system in order to provide for classification. In one embodiment, the image may be a whole slide image for pathology. In other cases, the image may be a digitized image from any source.

In still further cases, rather than image 310, another input type such as audio or video may be applied.

In order to analyze image 310, the image may be broken into a plurality of "patches" or tiles. Each tile/patch may, for example, represent 10 μm². However, this is merely an example and in other cases other sizes of patches may be applied. Further, in some case, instead of specifying the number of microns, the patch may be selected to be less than or equal to 1000×1000 pixels, or less than or equal to 400×400 pixels, or less than or equal to 256×256 pixels, or may be any other suitable number of pixels.

Further, in some cases, the tiles or patches do not need to be square and could be rectangular, circular, oval or more a complex shape.

Further, in some cases, the tiles may not be of the uniform size and shape. For example, one patch may be 400×400 pixels while another may be 300×300 or 300×200.

The size of the patches or tiles may be predetermined or may be dynamic based on information from a mask or based on the type of classification that is being performed and the type of image that is being input.

In some cases, the patches or tiles may be overlapping.

Each patch may then be processed as described below. However, supplementary information may be provided in conjunction with each patch in some cases to facilitate such processing. Specifically, in some cases, a mask 320 may be applied for processing concurrently with image 310.

For example, mask 320 may be a tumor mask that distinguishes between areas of normal cells in areas of cancerous cells. If a mask 320 is applied, generally the mask may be broken down into similar sized and configured patches as that of image 310. Therefore, a patch from the tumor mask or other such mask may be applied to a processing algorithm concurrently with the patch from image 310. The use of such mask may in some cases provide improved results. However, mask 320 is optional.

Each patch from image 310, possibly with a patch from mask 320, is applied to a neural network architecture 330. The neural network architecture 330 may for example be a convolutional neural network and may produce a one-dimensional vector output providing characteristics for each patch within the image 310.

One example of utilizing a convolutional neural network to process images is, for example, described in PCT Application Publication No. WO 2019/055555, entitled "Few-Shot Learning Based Image Recognition Of Whole Slide Image At Tissue Level", published Mar. 21, 2019, (the '555 application) the entire contents of which are incorporated herein by reference.

In the '555 application, computer vision is used to determine whether a sample is cancerous based on training from one or more pathologists as to whether one or patches of an image are positive or negative for a particular type or grade of cancer. The system utilizes a convolutional neural network (CNN), which is an artificial neural network which may be used in the field of computer vision. The CNN in the '555 application is provided with an input of an image of the tissue sample and the CNN may provide an output of a plurality of image feature values. In other words, feature extraction or feature representation of the visual descriptors is provided as an output. Such output would form a linear layer and may also be considered to be a one dimensional output.

As further described in the '555 application, prior to the CNN receiving an input of the relevant tissue sample, and providing an output of image feature values, in one embodiment the CNN may be trained on generic images. Such training may be used to allow for better outputs from the CNN.

Referring again to FIG. 3, one example of neural network architecture 330 is an Inception-v3 neural network architecture. This type of neural network architecture may, for example, produce an output of 2048 bits. As with the '555 application, the neural network architecture 330 may be trained on generic images or on specific slides prior to the use within categorization system of FIG. 3.

In some embodiments, the size of the vector produced by neural network architecture 330 may be too large. For example, if the vector is too large, the processing power required for subsequent elements within the system would be higher. Therefore, to enable an efficient system, in some cases, the size of the vector may need to be limited. In one case, Principal Component Analysis (PCA) 332 could further be applied to reduce the vector output size. For example, in one case, the use of PCA 332 could reduce the size of the output from 2048 bits to approximately 700 bits. Since the output must later be processed, for example utilizing a characterization or classification algorithm, a reduced bit size will facilitate such processing.

However, the use of PCA 332 is optional.

Further, in some cases, other neural network architectures could be utilized. For example, a ResNet34 deep residual learning algorithm may be utilized as neural network 330. Such algorithm may, for example, provide an output of 512 bits in some cases. In this case, a ResNet34 architecture could remove the need for PCA 332.

In other embodiments, other neural network architectures could be used for neural network architecture 330, and the present disclosure is not limited to any particular type of architecture.

The output from either neural network architecture 330 or from PCA 332 may then be applied to a classification algorithm in order to differentiate between the characteristics of each patch within the vector output. For example, in one embodiment of the present disclosure, the image may represent a whole slide image which may provide lung tissue to be analyzed. The lung tissue may be deemed as cancerous. However, there are two major histopathological subtypes for lung cancer, namely adenocarcinoma and squamous cell carcinoma. Therefore, a classification algorithm to accurately distinguish between these two types of lung cancers would be useful.

However, a single algorithm applied to all patches may not be as efficient as possible. In particular, in accordance with the embodiments described herein, depending on cell density a different classification algorithm may be applied to different patches to produce improved results.

In this regard, in the embodiment of FIG. 3, a density map 340 may be utilized to select a "bin" providing a classification algorithm for classifying the patch. The density map may provide, for example, a cell density for each patch and therefore enable the selection of the bin.

The density map may be created through a wide variety of techniques. In one case, the techniques provided in PCT publication number WO 2019/143633, "Real-Time Whole Slide Pathology Image Cell Counting", published Jul. 25, 2019, the entire contents of which are incorporated herein by reference, may be used. In that case, a plurality of patches comprising tissue areas are selected and stain intensity vectors are determined within the plurality of patches to generate a stain intensity image. The process then iteratively segments stain intensity images using a global threshold filter to generate a cell mask.

The process then applies a chamfer distance transform to the cell mask to generate a distance map, and a maximum height marker determined on the distance map is used to determine cell seeds.

The process then determines cell segments within the plurality of patches using a watershed transformation within the distance map and cell seeds as input.

A whole cell count is then calculated for the plurality of patches based on the cell segments.

In another example, the technique described in U.S. Pat. No. 9,466,009, entitled "Feature Density Object Classification, Systems and Methods" to Jaber at al., the contents of which are incorporated herein by reference, may be used to find a density map.

In other embodiments, other techniques for determining a density map may equally be utilized in association with the embodiments described herein.

Further, while the embodiment of FIG. 3 utilizes a density map as a characterization criterion, in other cases, density may not be the criteria used for characterization. Specifically, rather than density, other characteristics of the image may be utilized. For example, a brightness map may in some cases be utilized. In other cases, a contrast map, or other image differentiating characteristic map may be used.

In still other cases, some other characteristic map could be utilized to allow for the creation and utilization of a different bins. Specifically, if, instead of image 310, an audio input is provided, then rather than density map 340, a time map may be utilized in some cases. Other examples are possible.

Referring again to FIG. 3, in the example provided in the figure, a density map may be applied to select a bin. As used herein, a "bin" is a particular classification algorithm or module that is used to classify or categorize elements within the image patch. The algorithm can be any machine learning or predefined algorithm that would allow for the categorization based on the type of input and output provided for the system. For example, in the example of adenocarcinoma and squamous cell carcinoma classification, the bin can be a support vector machine (SVM) trained to distinguish between the two types of cells. Generally, the bin can include any linear and non-linear classifiers, including but not limited to Nearest Neighbors Classifier, Linear SVM Classifier, Radial-Basis Function kernel (RBF) SVM Classifier, Gaussian Process Classifier, Decision Tree Classifier, Random Forest Classifier, Neural Net Classifier, Deep Learning Classifiers, AdaBoost Classifier, Naive Bayes Classifier, Bayes Classifier, Gaussian Classifiers, Probabilistic Classifiers, Linear Discriminant Analysis/Classifier, and Quadratic Discriminant Analysis/Classifier, among others.

In other cases, other classification algorithms may be utilized. For example, a minimum-mean squared error (MSE) algorithm may be used in some cases.

In other cases, other classification algorithms could be used as would be apparent to those skilled in the art.

In the embodiment of FIG. 3, various bins are provided. In the example of FIG. 3, each bin provides a separate classification algorithm. For example, utilizing the cell classification case, the bins may provide linear and non-linear classifiers 350 for patches with a cell density of between 20 and 30 cells per patch. Linear and non-linear classifiers 352 may be provided for patches with a cell density of between 30 and 40 cells per patch. Other linear and non-linear classifiers, represented generically as classifiers 354, may further be provided for other densities. Finally, linear and non-linear classifiers 356 for a cell density greater than 110 is shown.

However, these bins are merely provided as an example, and those skilled in the art will appreciate that the bins can be divided based on the classification criteria, and may be optimized for the application that the classification system is being used for.

Therefore, the type and distribution of densities within the bins can vary based on the application.

Further, the number of bins used can vary based on the application. Thus, in one case, two or three bins may be sufficient. In other cases, 10 or more bins may be needed.

In some cases, the densities represented by successive bins may not be uniform. For example, a first bin may represent a difference of 25 cells per patch between the upper and lower bounds per patch while a second bin may represent a difference between the upper and lower bounds of 15 cells per patch.

In other cases, the bins may use a histogram distribution or statistical distribution rather than an even distribution.

Other examples are possible.

The characteristic determining module within the selected bin may then be applied to the patch to characterize the patch. For example, in the case of a determination between adenocarcinoma and squamous cell carcinoma, the patch may be analyzed based on the bin selected for the cell density, and a determination may be made as to the type of cancer cell within that patch.

The classification algorithm in each bin may be trained using samples having the same density as the associated bin. These training samples would include a known classification for the elements therein and would allow for the linear and non-linear classifiers to be optimized to provide for such classification.

The output from the bin is then provided to an image level result compiler 360, which may accumulate the results from each patch after it has been characterized, and then provide an overall characterization percentage for the image 310.

Therefore, utilizing the system of FIG. 3, each patch may be classified based on a characteristic of that patch and the results for the entire image may be compiled to provide for the classification of the image.

Figure 4:
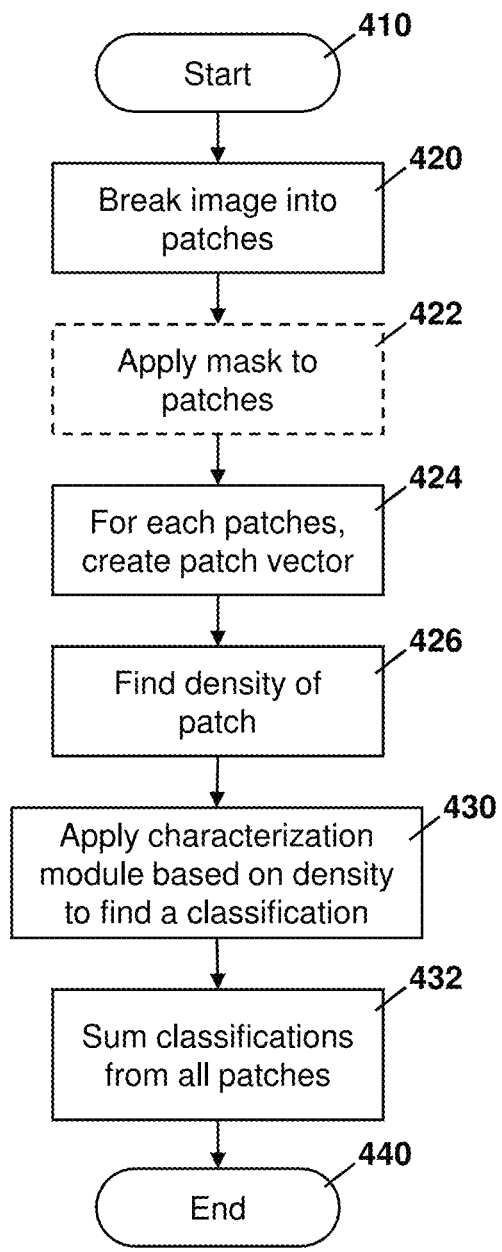
FIG. 4 is a process diagram showing a process for categorizing elements within an image.

A process for utilizing the system of FIG. 3 is shown with regard to FIG. 4. In particular, the process of FIG. 4 starts at block 410 and proceeds to block 420 in which an image is broken into patches. The patches may be divided based on an application into useful sizes and/or shapes.

The process then proceeds to block 422 in which a mask may optionally be applied to the patches. The mask would typically be divided into the same size and shape patches as the image and may provide additional information to a neural network or other vector creation algorithm.

From either block 420 or block 422, the process proceeds to block 424 in which, for each of the patches, a patch vector output is created. The patch vector output may then provide enough information for classification of the patch.

The process then proceeds to block 426 in which the density or other characteristic of the patch is found. This may be based on a density map as for example described with regard to block 340 from FIG. 3.

The process then proceeds to block 430 in which a bin based on the characteristic is selected for the particular patch. The bin contains a classification module or algorithm to allow for the classification of elements within the patch.

The process then proceeds to block 432 in which the classification for the particular class is added to a sum of classifications for all of the patches.

The process may continue to perform the steps from blocks 420 to block 432 until all of the patches for the image are processed.

The process then proceeds to block 440 and ends.

The system and process from FIGS. 3 and 4 may be applied to various circumstances. For example, as indicated above, the process may be up adapted to differentiate between adenocarcinoma and squamous cell carcinoma for lung cancer. In other cases, the classification may be between five different types of breast cancer cells. In other cases, a forest fire risk classification may be determined based on foliage density. In other cases, traffic monitoring and routing systems may be based on the vehicle density within roadways. In other cases, text density and word density may be used for language processing algorithms in a natural language processing scenario. In other cases, population counts utilizing density maps could occur. In other cases, a melanoma detector could utilize a scan of a person's body to characterize marks on the body. In other cases, in semiconductor manufacturing a defect detection system could utilize the techniques in the above disclosure. In further embodiments, structural analysis could be used to find cracks or voids in a structure from an image.

However, the above are merely examples of the various classification systems for which to the embodiments of FIGS. 3 and 4 could be applied and other applications of these embodiments would be apparent to those skilled in the art having regard to the present disclosure.

Some of these embodiments are described below.

Adenocarcinoma and Squamous Cell Carcinoma Differentiation for Lung Cancer Tumors One example of an application of the embodiments of FIGS. 3 and 4 is the automated classification of the type of lung cancer cell from diagnostic slide images. In particular, the most common form of lung cancer, non-small cell lung cancer, is further classified into two major histopathological types subtypes: adenocarcinoma and squamous cell carcinoma.

Classifying tumors accurately is important for prognosis and therapy decisions but requires costly pathologist review.

Figure 5:
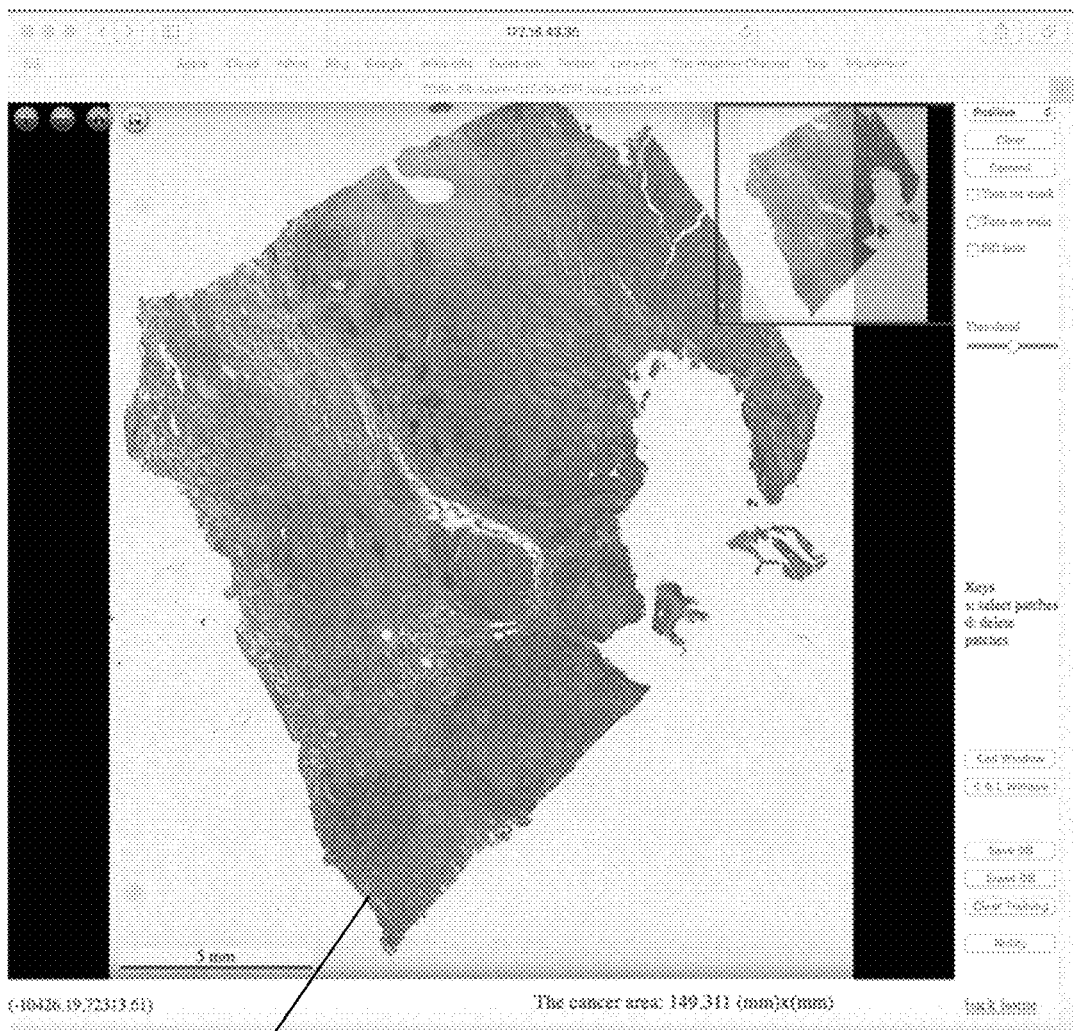
FIG. 5 is a graphical representation showing an example dyed tumor image.

In this regard, the system of FIG. 3 using whole slide images was trained to distinguish between adenocarcinoma and squamous cell carcinoma using cell density maps to choose a classification bin. Referring to FIG. 5, an expert guided tumor/normal masking procedure was created, in which a browser-based tool was developed to capture expert opinion on tumors or normal tissue points. These points were used to generate whole slide masks. The mask was then iteratively refined by selection of more tumors in normal points. In other words, human in the loop training occurred. FIG. 5 shows a hematoxylin and eosin (H&E) stained slide 510.

Figure 6:
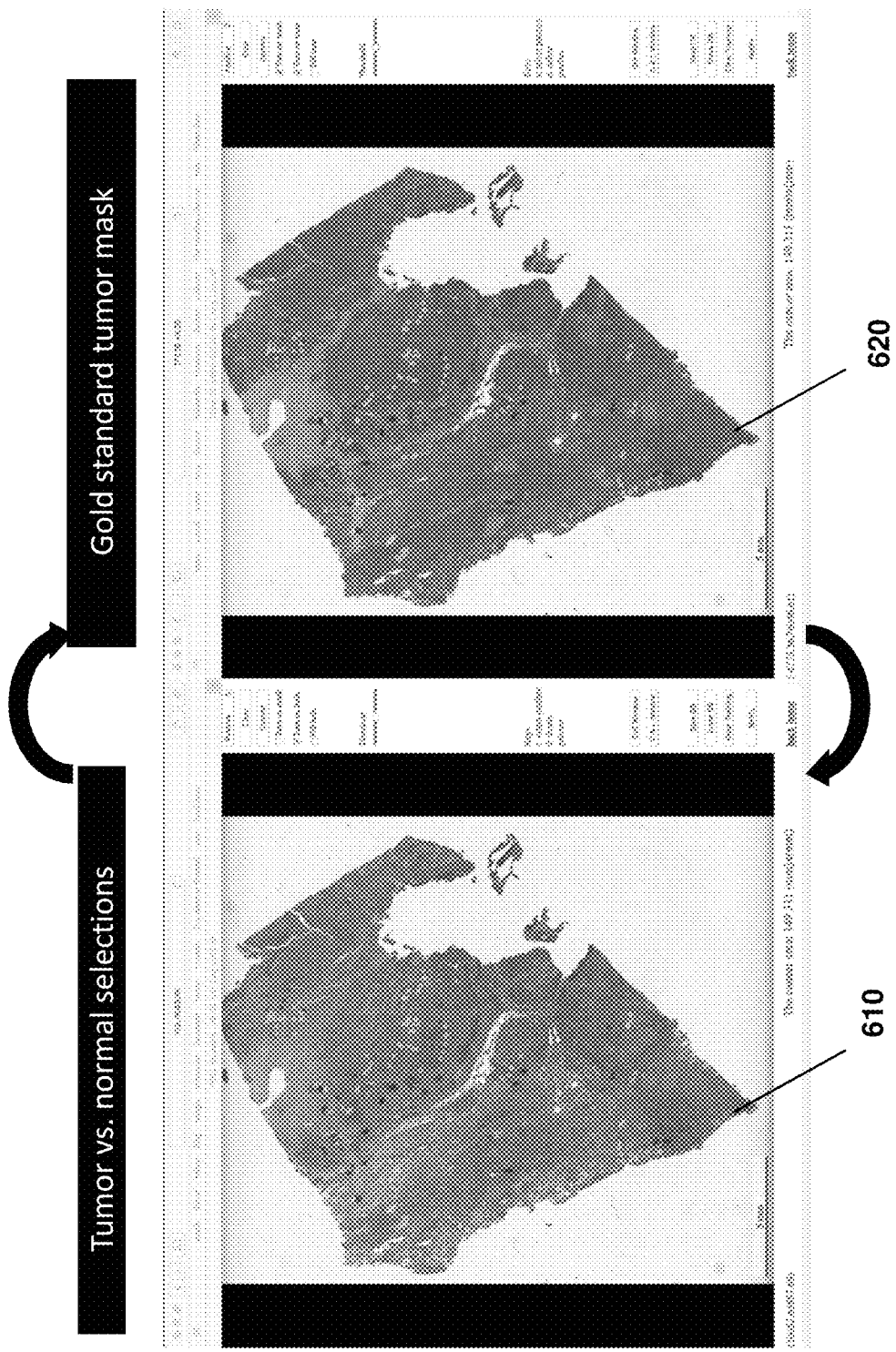
FIG. 6 is a graphical representation showing the development of a tumor mask.

FIG. 6 shows tumor versus normal selections mask 610 and a gold standard mask 620, which is iteratively worked towards. This resulted in the training of an expert system. In particular, a ResNet-34 was used.

Figure 7A:
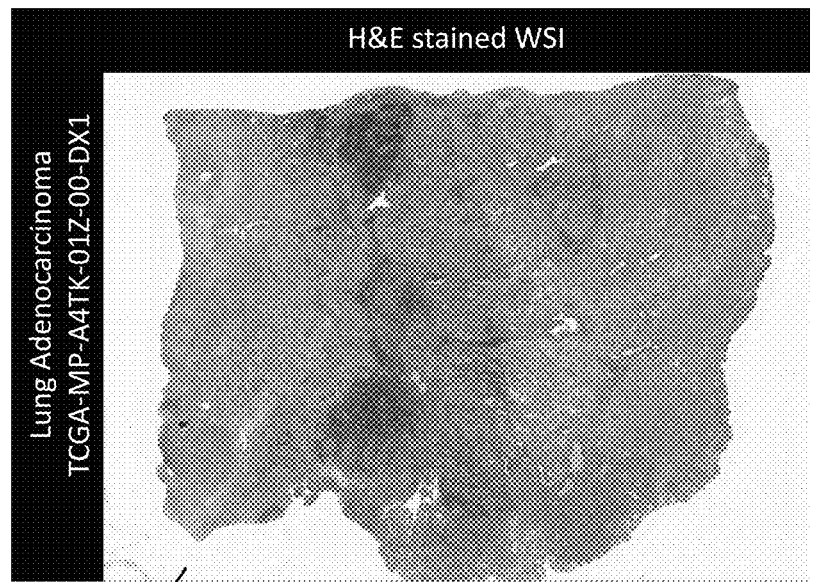
FIG. 7A is a graphical representation showing an H&E stained whole slide image of lung adenocarcinoma.
Figure 7B:
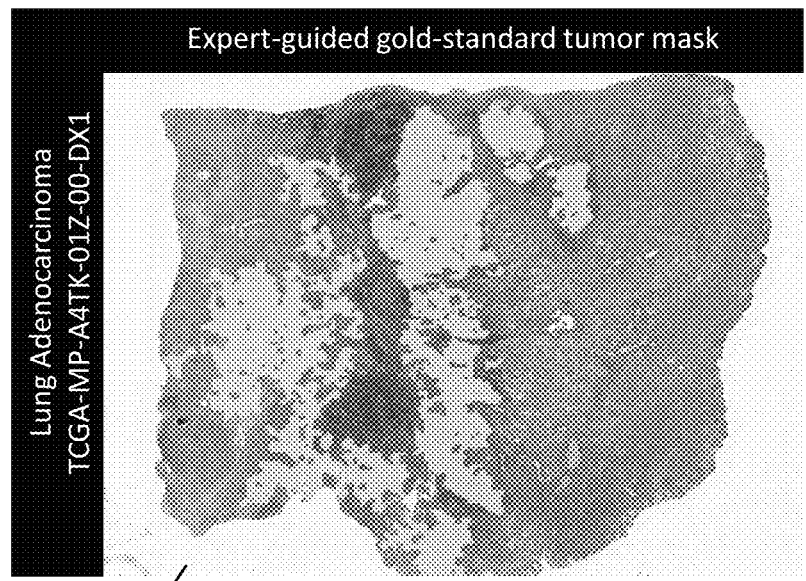
FIG. 7B is a graphical representation of a tumor mask of the slide of FIG. 7A created using the guidance of an expert.
Figure 7C:
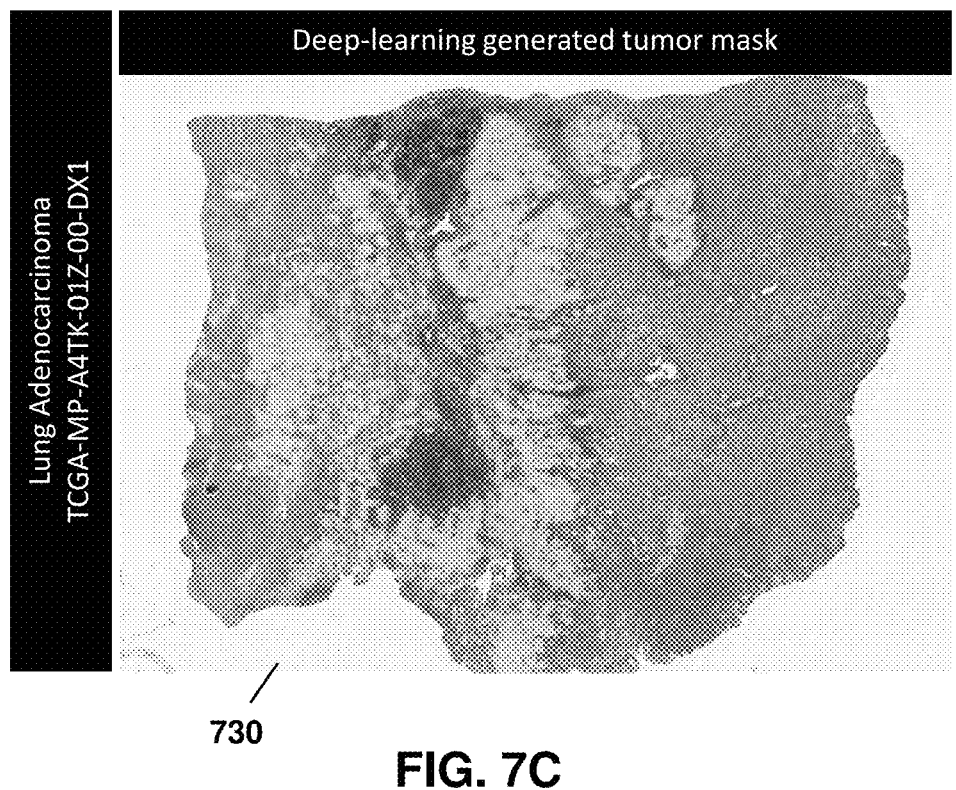
FIG. 7C is a graphical representation of a tumor mask of the slide of FIG. 7A created using a deep learning algorithm.

Reference is now made to FIGS. 7A to 7C. In the embodiment of FIG. 7A, a whole slide image 710 was used to create a tumor mask 720, shown in FIG. 7B, using expert guidance. Further, a deep-learning algorithm generated the tumor mask 730 of FIG. 7C.

Figure 8A:
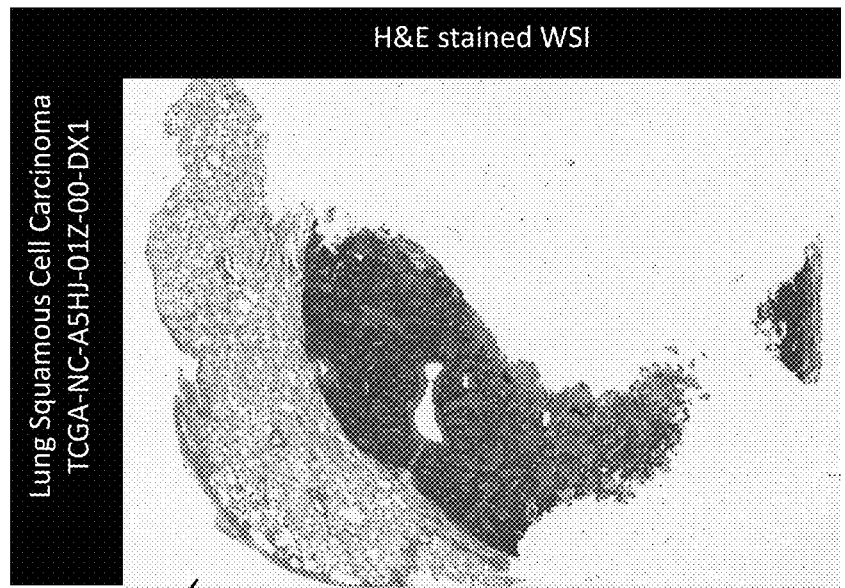
FIG. 8A is a graphical representation showing an H&E stained whole slide image of lung squamous cell carcinoma.
Figure 8B:
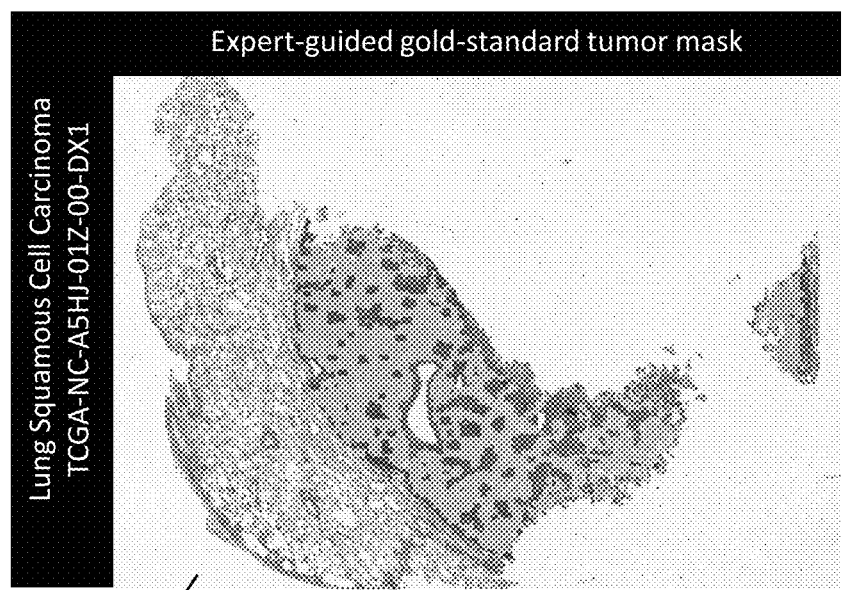
FIG. 8B is a graphical representation of a tumor mask of the slide of FIG. 8A created using the guidance of an expert.
Figure 8C:
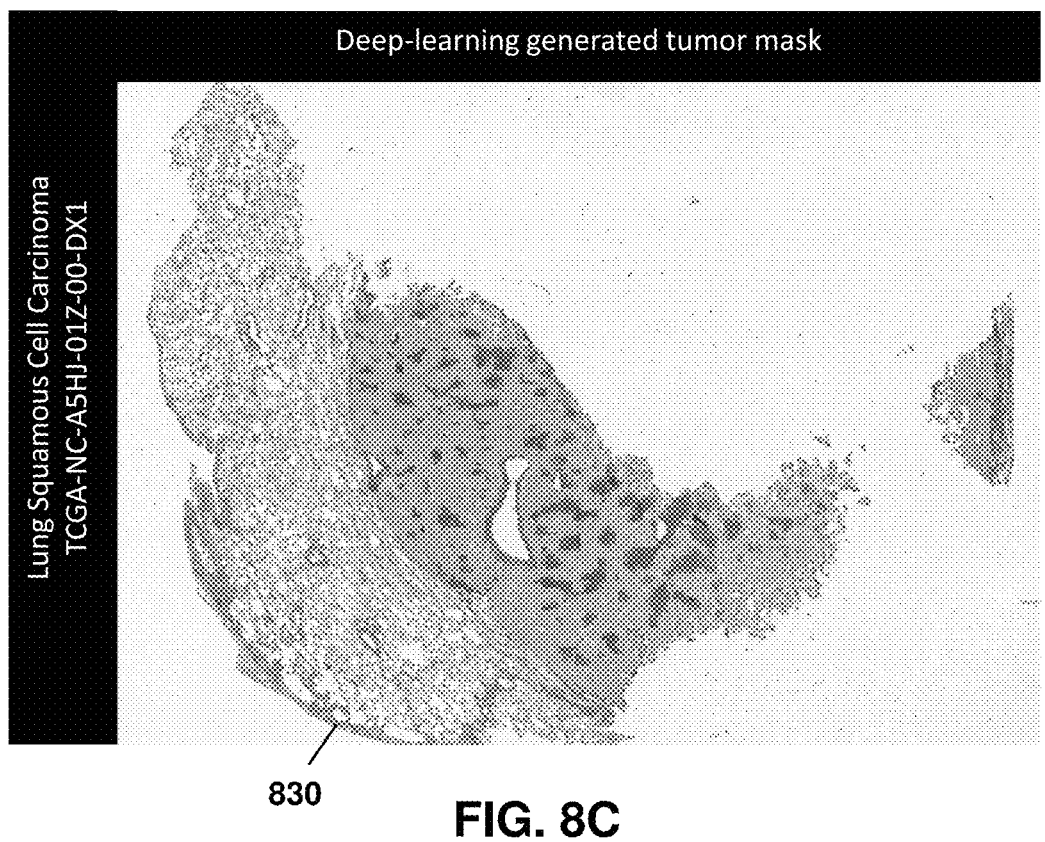
FIG. 8C is a graphical representation of a tumor mask of the slide of FIG. 8A created using a deep learning algorithm.

Similarly, for FIGS. 8A to 8C, a whole slide image 810 was used to create the expert guided tumor mask 820 in FIG. 8B. Further, a deep-learning algorithm generated a tumor mask 830 from FIG. 8C.

A further algorithm was trained to count cells in each to color patch. The cell counts system had modules for color deconvolution, local drain and watershed segmentation.

Figure 9A:
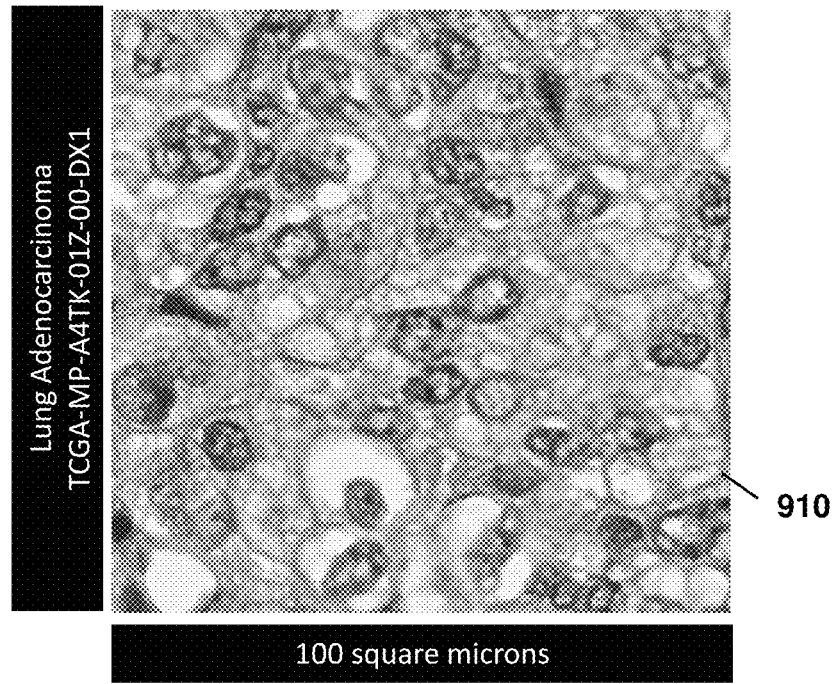
FIG. 9A is a graphical representation of a patch of an image showing lung adenocarcinoma.
Figure 9B:
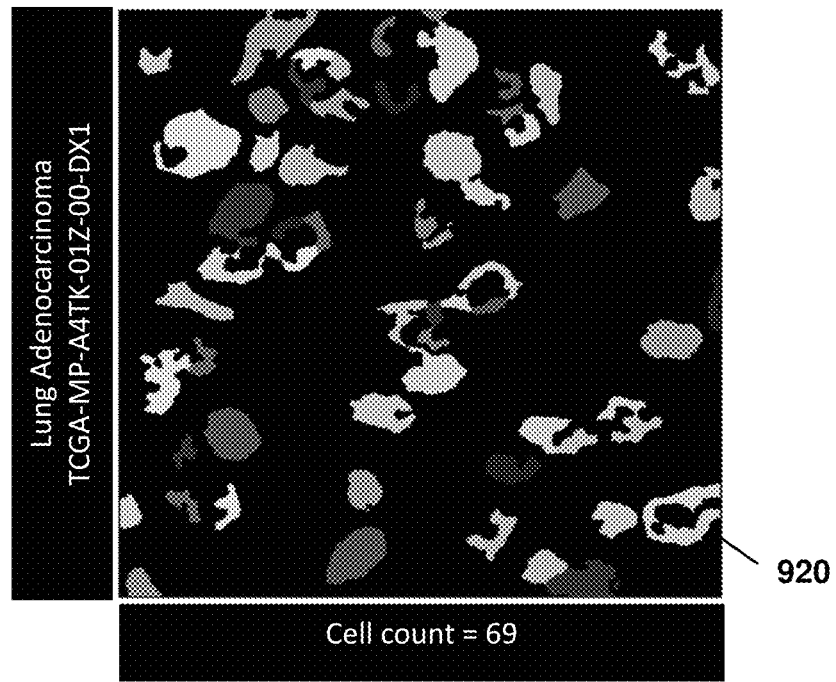
FIG. 9B is a graphical representation showing a cell count image for the patch of FIG. 9A.

Referring to FIG. 9A, the figure shows a patch 910 with a 100 μm$^2$ size. The algorithm was applied to patch 910 to produce the cell map 920 and provide a cell count of 69, as shown in FIG. 9B.

Figure 10A:
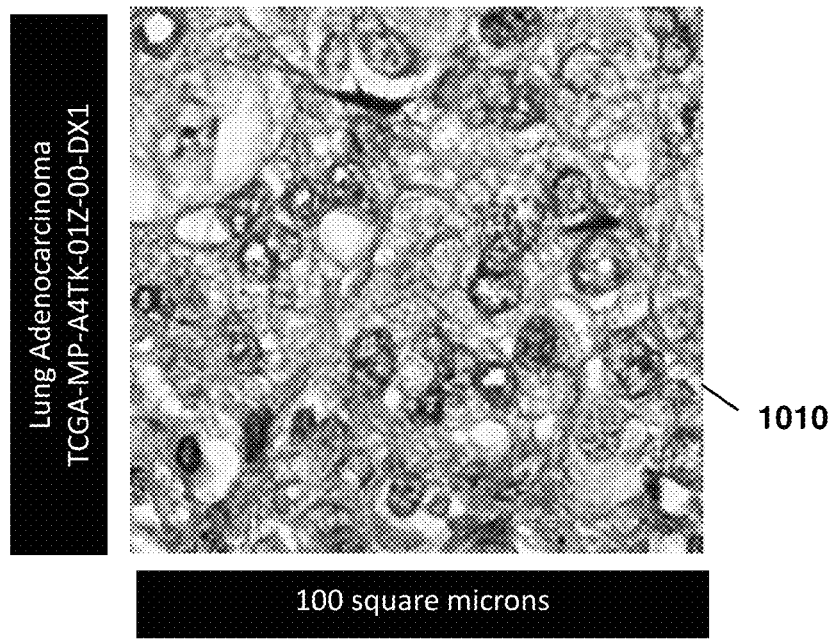
FIG. 10A is a graphical representation of a patch of an image showing lung adenocarcinoma.
Figure 10B:
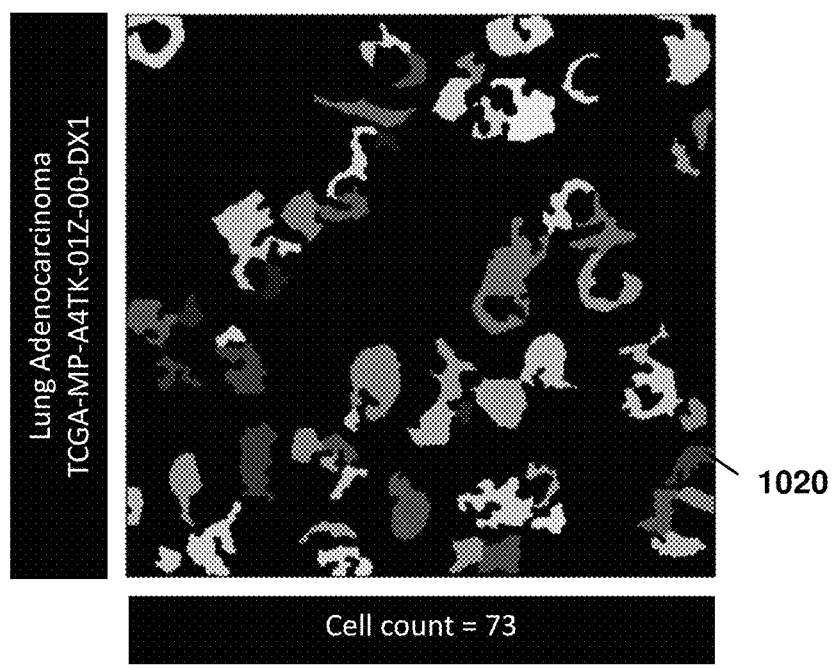
FIG. 10B is a graphical representation showing a cell count image for the patch of FIG. 10A.

Similarly, referring to FIG. 10A, the figure shows a patch 1010 with a 100 μm$^2$ size. The algorithm was applied to patch 1010 to produce cell map 1020 in FIG. 10B and provide a cell count of 73.

Figure 11A:
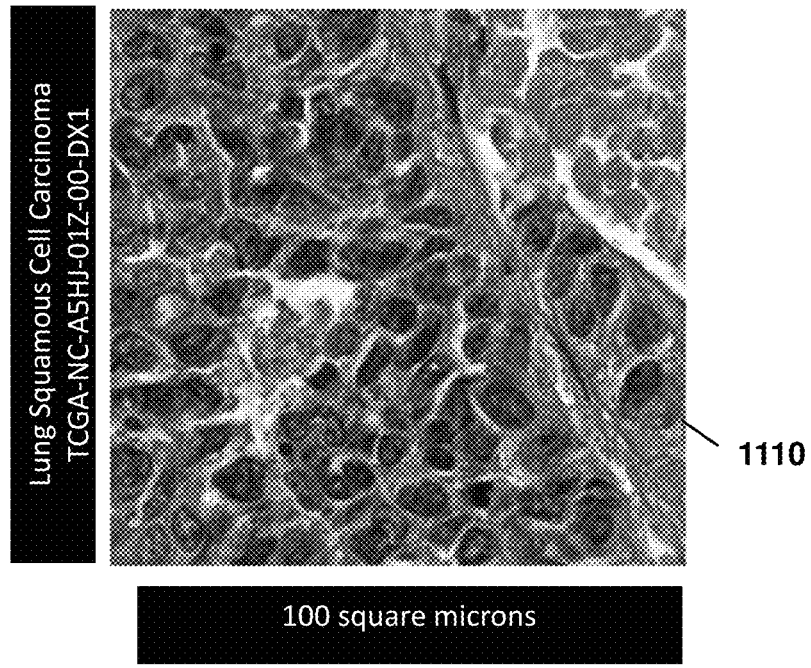
FIG. 11A is a graphical representation of a patch of an image showing lung squamous cell carcinoma.
Figure 11B:
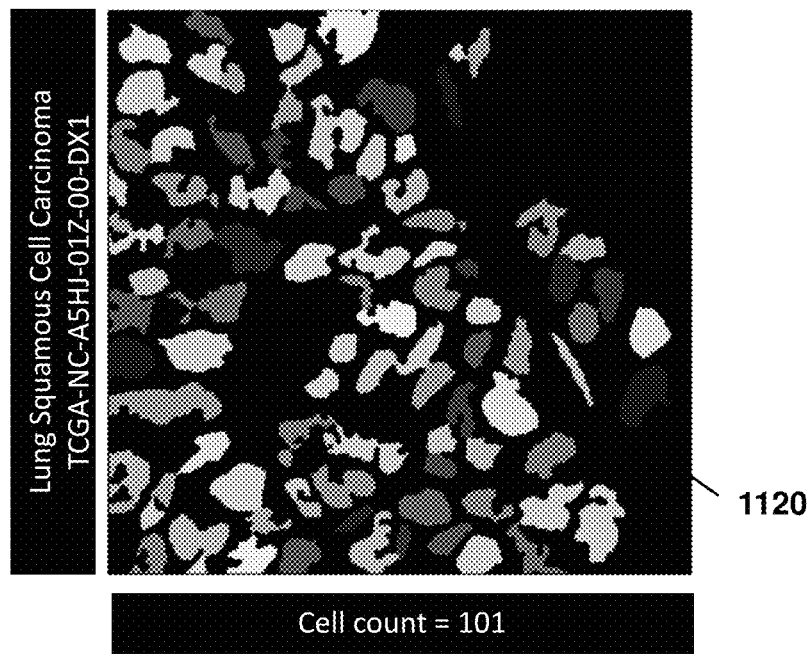
FIG. 11B is a graphical representation showing a cell count image for the patch of FIG. 11A.
Figure 12A:
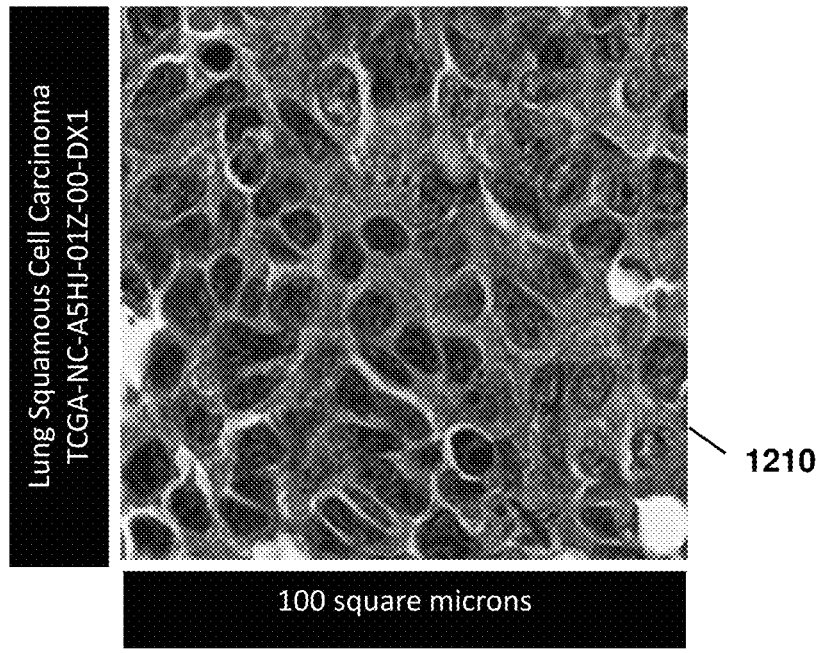
FIG. 12A is a graphical representation of a patch of an image showing lung squamous cell carcinoma.
Figure 12B:
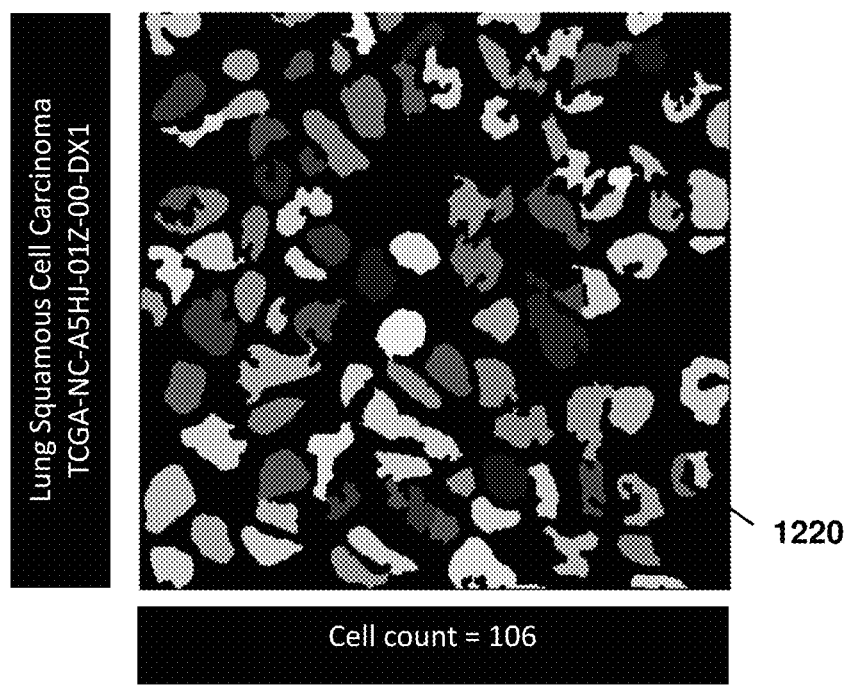
FIG. 12B is a graphical representation showing a cell count image for the patch of FIG. 12A.

Referring to FIG. 11A, the figure shows a patch 1110 with a 100 μm$^2$ size. The algorithm was applied to patch 1110 to produce cell map 1120 in FIG. 11B and provide a cell count of 101.

The patches, such as those shown in FIGS. 7A and 7C and 8A and 8C, were then used to create one dimensional descriptive vectors of the 100 μm$^2$ color patches in the target whole slide image. Further, the patches such as those described in FIGS. 9A and 9B, 10A and 10B, and 11A and 11B were then applied as the cell density maps into the system of FIG. 3.

In this example, 10 discrete bins were defined, and the density maps were used to classify each patch into one of these bins based on the cell density within that patch.

10 adenocarcinoma/squamous cell carcinoma linear SVM classifiers (one for each cell-density bin) were trained on the transformed data.

Tests were then performed on training sets. In particular, 150 test whole slide images were used in evaluation. In a first instance, all valid patches of a test WSIs were used. In other words, the entire WSI was considered to be a tumor.

In a second test, tumor patches of the test WSIs were used based on the deep learning framework of FIGS. 7A, 7C, 8A and 8C.

Figure 13:
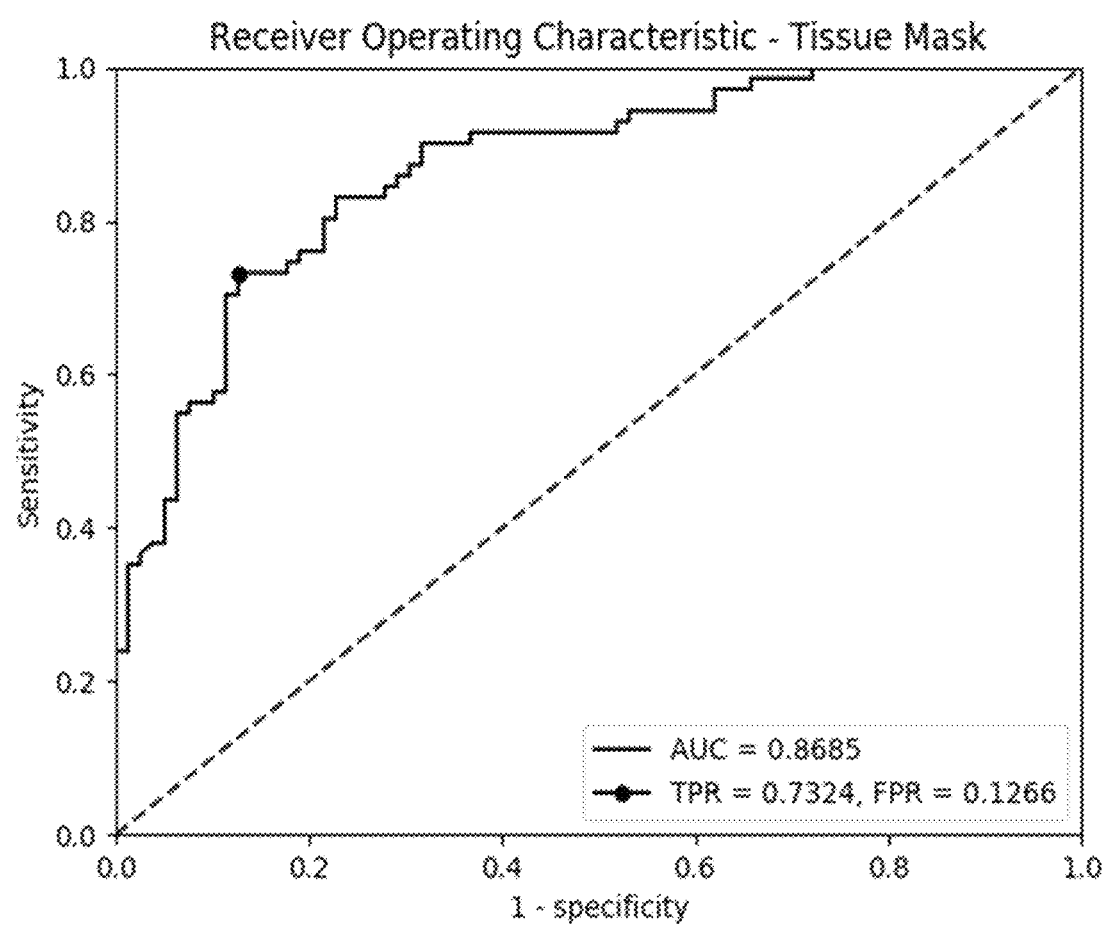
FIG. 13 is a plot showing a receiver operating characteristics curve when all valid patches of the test whole slide images are used in one example.
Figure 14:
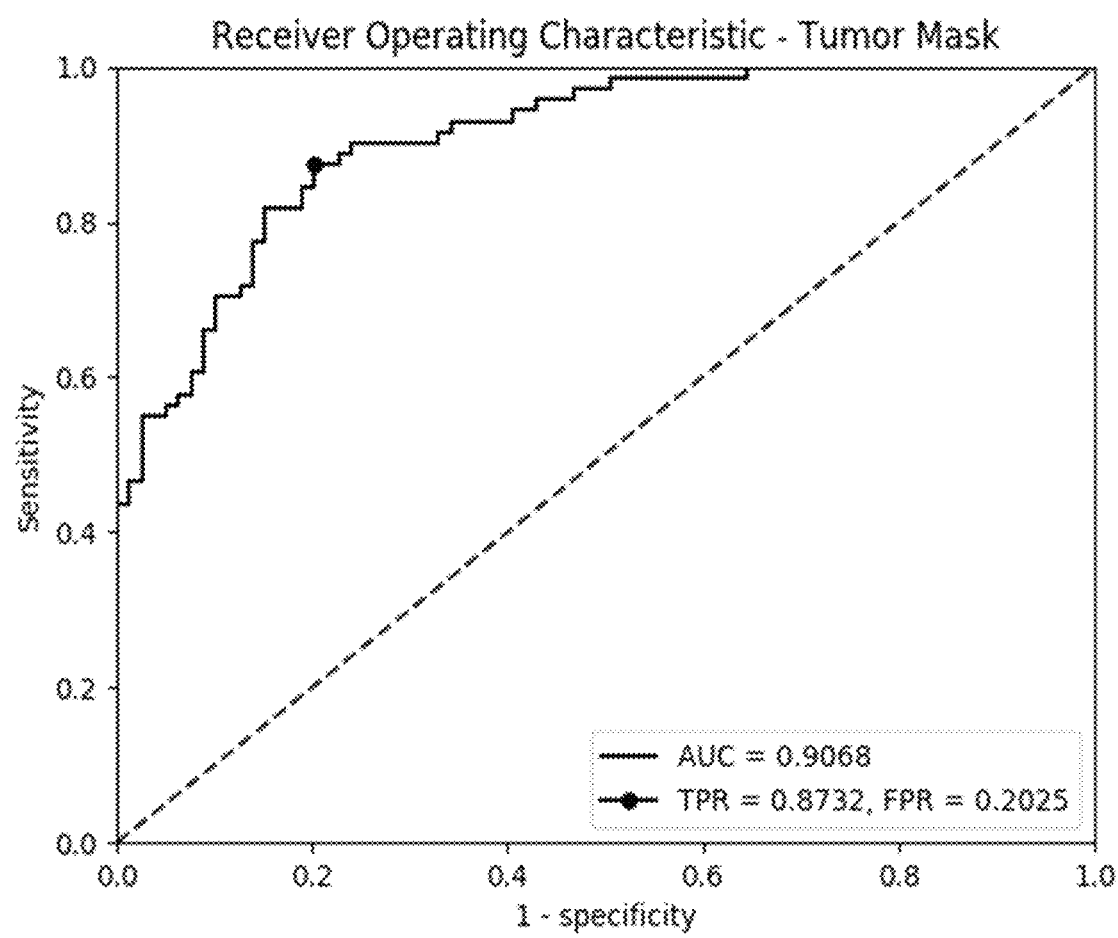
FIG. 14 is a plot showing a receiver operating characteristics curve when tumor patches of test images were used in the embodiments of the present disclosure.
Figure 15:
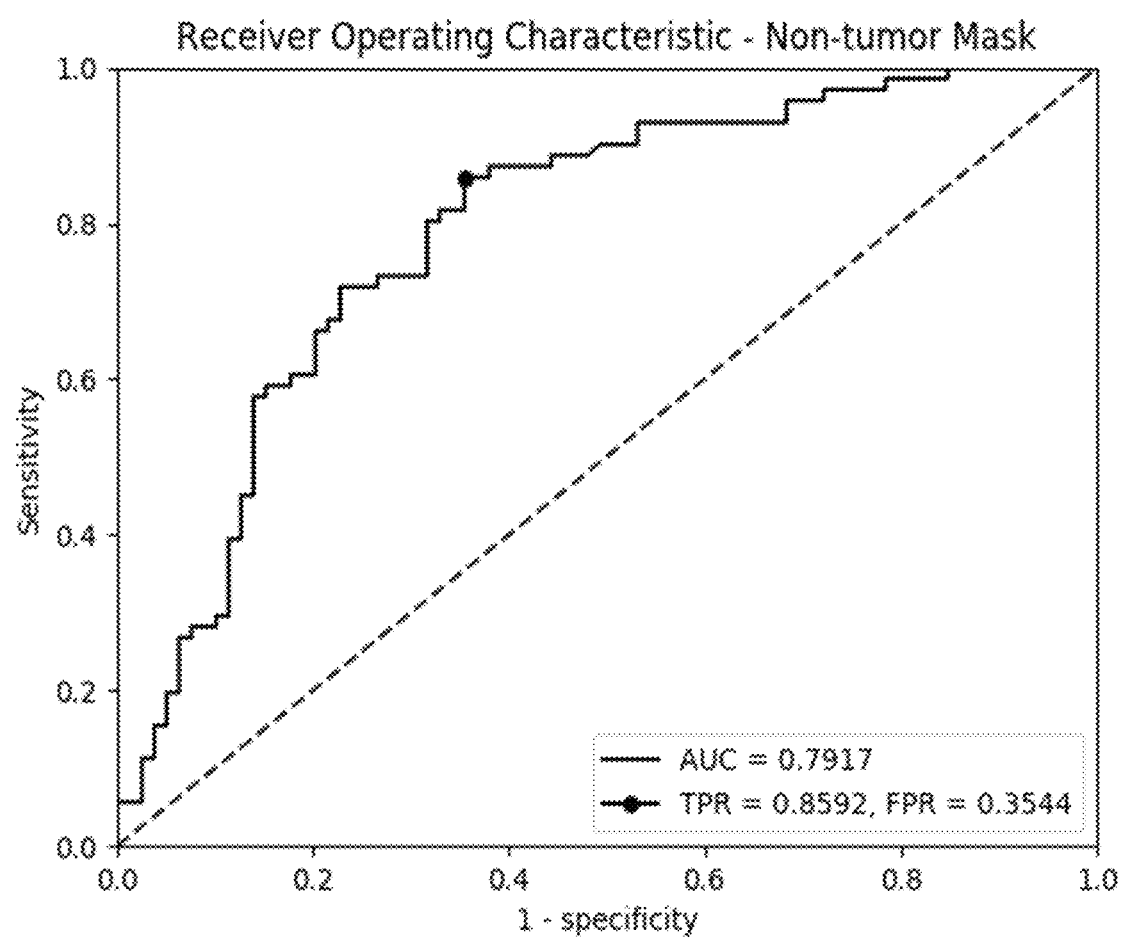
FIG. 15 is a plot showing a receiver operating characteristics curve of adjacent normal patches alone in accordance with the embodiments of the present disclosure.

The results of the classification are, for example, shown in a plurality of receiver operating characteristic (ROC) curves. For example, FIG. 13 shows an ROC curve when no tumor mask was used, FIG. 14 shows an ROC curve when tumor patches of test WSIs were used, and FIG. 15 shows an ROC curve when adjacent normal patches alone were used.

The performance is illustrated in Table 1 below.

From Table 1 above, when used for classification of non-small cell lung cancer, the algorithm as described herein showed comparative or better performance while maintaining higher spatial resolution of tissues used to give overall adeno/squamous cell in test images.

An automated non-small cell lung cancer subtype classifier based on cell-count based tumor patch was thus developed by training on an expert system and utilizing a method of cell density mapping.

The embodiments achieved an area under the ROC Curve of 0.9068 in test samples, corresponding to a classification accuracy of 83.33%. Further, the (heretofore excluded) adjacent normal regions were classified correctly and almost as accurately as tumor regions (74.7%).

This fully-automated histopathology-based subtyping classifier generates maps of regions-of-interest within WSIs, providing novel spatial information on tumor organization. For example, the results indicated above on test data show tumor patches of 100 square microns in size with 60 to 100 cells distinguish adenocarcinoma from squamous cell carcinoma better than other cell-density ranges. Moreover, this classifier reveals that adjacent normal tissue may provide additional insights into tumorigenesis/invasion mechanisms.

This deep-learning system outperforms similar efforts using CellProfiler features as for example described in Yu, K.-H. et al. *Predicting non-small cell lung cancer prognosis by fully automated microscopic pathology image features.* Nature Communications, Vol. 7, Article number: 12474 (2016), and provides additional explanatory information beyond systems with similar performance, for example as described in Coudray, N. et al. *Classification and mutation prediction from non-small cell lung cancer histopathology images using deep learning*, Nature Medicine, Vol. 24, pages 1559-1567 (2018).

Breast Cancer Classification

In a further embodiment, rather than distinguishing between two types of cancer cells in a whole slide image showing non-small cell lung cancer cells, the same technique may be applied to breast cancer cell classification.

In particular, an image showing a breast cancer tumor may contain various types of cancer cells. For example, in some embodiments, four or five different types of cancer cells may exist within such tumor.

TABLE 1

Performance of The Present Classifier System Relative To Other State-Of-The-Art Methods

| Test set | | Patch size in square microns | Average number of test patches in WSI | Area under the ROC Curve | Accuracy |
|---|---|---|---|---|---|
| Yu, K.-H. et al. (2016) Train and test on TCGA diagnostic & frozen tissue WSIs | | 250 | 10 | 0.7500 | — |
| Coudray, N. et al. (2018) Train on TCGA frozen tissue WSIs and test on diagnostic WSIs | | 256 | — | 0.8825 | — |
| | | 1024 | — | 0.9180 | — |
| Graham, S. et al. (2018) - 64 WSIs from 2017 Computational Precision Medicine Challenge | | 256 | 2056 | — | 81.00% |
| Embodiments from the present disclosure | Test using all tissues | 100 | 14906 | 0.8685 | 80.67% |
| | Test using tumor mask | 100 | 6,722 | 0.9068 | 83.33% |
| | Test using adjacent normal mask | 100 | 8,184 | 0.7917 | 74.67% |

In this regard, the system of FIG. 3 and the process of FIG. 4 could be utilized to provide for a four or five way classification. The process and system would use the same inputs and, in this case, the bins would include classification modules adapted to provide four or five way classifications. Thus, again based on the cell density, the patch could be applied to one of a plurality of SVMs or other linear and non-linear classification modules and an output from that SVM or classification module could indicate that the patch contained in a particular type of cancer cell.

The compilation module could then compile the results from the plurality of bins for the plurality of patches to give an indication of the breast cancer type.

In other cases, other cancer types could also be classified.

Forest Fire Risk Classification

In still a further embodiment, rather than a whole slide image, satellite images or aerial images of wilderness may be used to classify the forest fire risk in those areas. In this case, the characteristic map that is used to select the classification bin may be based on the density of the foliage within a particular patch of the satellite or aerial image. In other cases, the characteristic may be based on a predominant color within a particular patch. Other characteristics could also be used.

Each patch could then be evaluated for a forest fire risk utilizing the classification algorithm within the selected bin.

Thereafter, the forest fire risk may be calculated for various regions and resources dispatched based on such calculated forest fire risk.

Structural Analysis

In still a further embodiment, rather than a still image, a video image of a building may be processed utilizing a system such as that described above with regard to FIG. 3. Still frames from the video or consecutive frames from the video may for example be analyzed for defects within a structure such as cracks or voids or looking at welds within a metal framework.

In this case, the characterization may be based on a material type in order to find a bin with a classification algorithm.

The results of the analysis could then be compiled, and areas of concern can be flagged for further analysis or investigation in some cases.

Other Input Sources

While the above examples all provide for image inputs, in other cases, other types of inputs may be provided to the system of FIG. 3. In particular, in some cases a rater or 3-D image may be provided to the system. Further, in some cases audio may be provided to the system. Other options are also possible.

Depending on the type of input, the characterization criteria used for the of a classification bin may vary. For example, rather than a density map, in some cases a time map may be utilized. In other cases, the density map may be three-dimensional. Other options are possible.

Based on the above, various features or clusters the features may be utilized to provide for characterization of the image or input source in order to then allow for the classification algorithm to be properly selected from among a plurality of bins of classification algorithms.

In practical tests, when comparing the performance of stack of classifiers based on cell-density to baseline system which combined data from all cell-densities into one big classifier, the results were consistent for different setups. That is, the stack of classifiers based on cell-density outperformed the corresponding baseline system in terms of classification accuracy and time to build the classifiers.

Tests were performed for 2-ways, 3-ways, and 4-ways linear and nonlinear classifiers which includes SVMs, Neural Networks, Decision Tree, and k-nearest neighbors' algorithms. The result favored using a stack of classifiers based on cell-densities.

2-ways tests used lung cancer image data from the Cancer Genome Atlas (TCGA). One system used diagnostic images from Formalin-Fixed Paraffin-Embedded (FFPE), and the another used flash frozen images. The two classes used in building diagnostic-based SVMs and frozen-based SVMS were Lung Squamous Cell Carcinoma (LUSC) and Lung Adenocarcinoma (LUAD).

3-ways classifiers used breast cancer diagnostic images from TCGA. The three classes were Luminal A (About 30-45 percent of breast cancers are luminal A tumors), Luminal B (About 10-20 percent of breast cancers are luminal B tumors), and Triple-negative/basal-like (About 15-20 percent of breast cancers are triple negative/basal-like).

4-ways classifiers used breast cancer diagnostic images from TCGA. The four classes were Luminal A, Luminal B, Triple-negative/basal-like, and HER2-enriched (About 5-15 percent of breast cancers are HER2-enriched subtype).

Tests were also run with different image patch-size, including 100 square micron, 200 square micron, 300 square micron, and 1 square mm patch sizes. For the tests conducted, it was found that the best performance in lung cancer was when patch size=1 square mm patch (1000 square micron) with AUC Micro=0.9440 (& AUC Macro=0.9509) while breast cancer subtyping systems exceled at 100 square micron patch size with AUC Micro=0.8417 (& AUC Macro=0.8160) for 3-ways system and AUC Micro=0.8337 (& AUC Macro=0.7932) for 4-ways system.

A further test on breast cancer image data was performed balancing the number of train patches per subtype in the SVMs. The overall result/performance for this setup was better than the corresponding baseliner system, but inferior to system without train data balance.

One last test was done without the use of (optional) input tumor mask on lung data (one system using diagnostic WSI and the other using flash frozen images). In these systems, again, using a stack of classifiers based on cell densities outperformed the corresponding baseline system which accumulate all patched data in one big classifier.

Based on this, the use of features or clusters the features to provide for characterization of the image or input source in order to then allow for the classification algorithm to be properly selected from among a plurality of bins of classification algorithms exceeded baseline model performance.

The structure, features, accessories, and alternatives of specific embodiments described herein and shown in the Figures are intended to apply generally to all of the teachings of the present disclosure, including to all of the embodiments described and illustrated herein, insofar as they are compatible. In other words, the structure, features, accessories, and alternatives of a specific embodiment are not intended to be limited to only that specific embodiment unless so indicated.

Furthermore, additional features and advantages of the present disclosure will be appreciated by those skilled in the art.

The invention claimed is:

1. A method at a computing device for classifying elements within image data of a histopathology slide, the method comprising:

breaking the image data into a plurality of patches, each patch of the plurality of patches corresponding to a portion of the image data;

for each patch:
creating a vector output;
applying a density map to obtain a cell density;
selecting a classification bin from a plurality of classification bins according to the cell density, wherein each of the plurality of classification bins corresponds to a different density range for the element; and
utilizing the selected classification bin to classify the vector output to create a classified output; and
compiling the classified output from each patch.

2. The method of claim 1, further comprising applying a mask to the image data prior to creating the vector input.

3. The method of claim 1, wherein the creating the vector output is performed using a convolutional neural network.

4. The method of claim 1, wherein each classification bin from the plurality of classification bins contains linear and non-linear classifiers.

5. The method of claim 4, wherein the linear and non-linear classifiers in each classification bin are optimized based on the density map.

6. The method of claim 1, wherein the image data comprises an image of a tumor.

7. The method of claim 6, wherein each classification bin contains linear and non-linear classifiers to identify between different types of cancer cells at a cell density level associated with the classification bin.

8. The method of claim 7, wherein the tumor is a non-small cell lung cancer and the different types of cancer cells include adenocarcinoma and squamous cell carcinoma cells.

9. The method of claim 8, further comprising applying a tumor mask to the image data.

10. The method of claim 7, wherein the tumor is a breast cancer and the different types of cancer cells can be divided into two or more of: Luminal A, Luminal B, Triple-negative/basal-like, and HER2-enriched cells.

11. A computing device for classifying elements within image data of a histopathology slide, the computing device comprising a processor configured to execute instructions to:
break the image data into a plurality of patches, each patch of the plurality of patches corresponding to a portion of the image data;
for each patch:
create a vector output;
apply a density map to obtain a cell density;
select a classification bin from a plurality of classification bins according to the cell density, wherein each of the plurality of classification bins corresponds to a different density range for the element; and
utilize the selected classification bin to classify the vector output to create a classified output; and
compile the classified output from each patch.

12. The computing device of claim 11, wherein the computing device is further configured to utilize a mask for the image data prior to creating the vector input.

13. The computing device of claim 11, wherein the vector output is created using a convolutional neural network.

14. The computing device of claim 11, wherein each classification bin from the plurality of classification bins contains linear and non-linear classifiers.

15. The computing device of claim 11, wherein the linear and non-linear classifiers in each classification bin are optimized based on the density map.

16. The computing device of claim 11, wherein the image data comprises an image of a tumor.

17. The computing device of claim 16, wherein each classification bin contains a support vector machine to identify between different types of cancer cells at a cell density level associated with the classification bin.

18. The computing device of claim 17, wherein the tumor is a non-small cell lung cancer and the different types of cancer cells include adenocarcinoma and squamous cell carcinoma cells.

19. The computing device of claim 18, wherein the processor is further configured to execute instructions to apply a tumor mask to the whole slide image.

20. The computing device of claim 17, wherein the tumor is a breast cancer and the different types of cancer cells can be divided into two or more of: Luminal A, Luminal B, Triple-negative/basal-like, and HER2-enriched cells.

21. A non-transitory computer readable medium for storing instruction code for classifying elements within an input, which, when executed by a processor of a computing device cause the computing device to:
break the image data into a plurality of patches, each patch of the plurality of patches corresponding to a portion of the image data;
for each patch:
create a vector output;
apply a density map to obtain a cell density;
select a classification bin from a plurality of classification bins according to the cell density, wherein each of the plurality of classification bins corresponds to a different density range for the element; and
utilize the selected classification bin to classify the vector output to create a classified output; and
compile the classified output from each patch.

* * * * *